(12) United States Patent
Hoffman

(10) Patent No.: US 7,816,343 B2
(45) Date of Patent: Oct. 19, 2010

(54) WOOD PRESERVATIVE COMPOSITION

(75) Inventor: Mark C. Hoffman, Mosinee, WI (US)

(73) Assignee: HWD Acquisition, Inc., Medford, WI (US)

( * ) Notice: Subject to any disclaimer, the term of this patent is extended or adjusted under 35 U.S.C. 154(b) by 813 days.

(21) Appl. No.: 11/715,570

(22) Filed: Mar. 8, 2007

(65) Prior Publication Data

US 2008/0221067 A1 Sep. 11, 2008

(51) Int. Cl.
*A01N 59/14* (2006.01)
*A01N 55/08* (2006.01)
*A01N 43/653* (2006.01)
*A01N 47/10* (2006.01)
*A01N 37/08* (2006.01)

(52) U.S. Cl. .................. 514/64; 514/383; 514/479; 514/521; 514/531; 424/659; 424/660

(58) Field of Classification Search .................. 424/659, 424/660; 514/64, 383, 479, 521, 531
See application file for complete search history.

(56) References Cited

U.S. PATENT DOCUMENTS

| | | | |
|---|---|---|---|
| 4,879,083 A | 11/1989 | Knudson et al. | |
| 4,911,988 A | 3/1990 | Cass et al. | |
| 4,950,685 A | 8/1990 | Ward | |
| 5,151,127 A | 9/1992 | Thompson | |
| 5,389,300 A | 2/1995 | Schmitt et al. | |
| 5,480,638 A | 1/1996 | Erwin | |
| 5,516,620 A | 5/1996 | Cheng et al. | |
| 5,575,996 A | 11/1996 | Erwin | |
| 5,763,338 A | 6/1998 | Sean | |
| 5,846,305 A | 12/1998 | Payzant | |
| 5,880,142 A | 3/1999 | Otsu et al. | |
| 5,916,356 A | 6/1999 | Williams et al. | |
| 5,972,266 A | 10/1999 | Fookes et al. | |
| 5,990,043 A | 11/1999 | Kugler et al. | |
| RE36,798 E | 8/2000 | Williams et al. | |
| 6,416,789 B1 | 7/2002 | Marks et al. | |
| 6,582,732 B1 | 6/2003 | Bender et al. | |

OTHER PUBLICATIONS

Exhibit A, Natural England; "Remedial timber treatment products suitable for use in bat roosts", pp. 1-8.
Exhibit B, Triton Tripaste PB; "Deeply Penetrating Timber Preservative Paste", pp. 1-3.
Exhibit C, Palace Chemicals; "Ecology Fungicide Insecticide".
Exhibit D, Sealocrete; "Timber Master Wood Preserver".

*Primary Examiner*—John Pak
(74) *Attorney, Agent, or Firm*—Merchant & Gould P.C.

(57) ABSTRACT

A wood preservative composition comprising a mixture of a fungicide which is a combination of a boric acid ester, which is soluble in an organic solvent and has a sterically hindered di-alcohol or tri-alcohol group, such as trihexylene glycol biborate, an organo-iodine compound, a triazole, and a synthetic pyrethroid insecticide, said fungicide and the insecticide being present in a sufficient amount that wood treated with the wood treatment material contains fungicide and insecticide in an amount of about 1 ppm to 5000 ppm, based on the weight of the wood after treatment.

15 Claims, No Drawings

WOOD PRESERVATIVE COMPOSITION

BACKGROUND OF THE INVENTION

This invention relates to an improved, organic solvent based, wood preservative composition which provides improved stability, which includes a combination of a fungicide, including a boron-containing compound, at least one triazole compound, and an organo iodine compound, an insecticide, including a synthetic pyrethroid, and optionally water repellants and/or other organic insecticides, and which provides resistance to insect attack on wood treated with this combination.

Wood and wood-based materials, including cellulosic composites and plastic-wood composites, are susceptible to damage from insect pests including ants, beetles and termites. The Formosan subterranean termite, *Coptotermes formosanus* Shiraki, is of particular concern since this termite species is the most widely distributed and damaging termite pest in tropical and subtropical regions of the world. It is responsible for tens of millions of dollars each year in costs of damages and control in the State of Hawaii, and it is an increasingly serious problem across the southern United States. The rapid feeding rate, large colony size and aggressive foraging of this termite species make it especially challenging with respect to effective wood treatment substances for protecting wood and wood products from attack by this particular pest.

A variety of fungicides including or combined with boron compounds have been used to protect wood and wood composites from decay. For example, it is known to use zinc borate to protect cellulosic composites, including particleboard, hardboard and oriented strand board, from fungal decay, as described in U.S. Pat. Nos. 4,879,083; 5,763,338; and 5,972,266. Zinc borate is usually applied as a powder or a liquid suspension to wood chips or strands, prior to their fabrication into panels. However, zinc borate is not a very cost-effective wood preservative, and does not provide good protection against mold, mildew and staining fungi at typical use levels.

Boric acid forms white, needlelike crystals in which the B(OH)3 units are linked together by hydrogen bonds to form layers of nearly hexagonal symmetry. The boric acid crystals are not very soluble, and in fact, the solubility of boric acid in cold water is only about 63.5 grams/liter at room temperature. So, saturated aqueous solutions of boric acid can contain no more than about one percent-by-weight boron. Liquid boron solutions have been prepared by dissolving an inorganic borate, e.g., sodium borate, in water. Because the borates are not significantly more soluble than boric acid, the maximum concentration of boron which can be achieved with saturated borate solutions is only about three percent-by-weight. See, for example, the Handbook of Chemistry and Physics, $54^{th}$ Edition, CRC Press, Cleveland, Ohio, pages B-74 and B-136.

Other attempts to increase the concentration of boron in solution have involved the reaction of boron compounds, e.g., boric acid and the borates, with polyamines and alkanolamines to produce polyborates. Because these polyborates are more soluble in water, aqueous solutions containing higher boron concentrations may be prepared.

Other examples of boron containing compositions have been suggested for use as wood preservatives include U.S. Pat. No. 4,911,988 which teaches the use of boro-organic ester compounds to make shaped elements that are inserted into the preformed cavities in timber or other materials. U.S. Pat. No. 6,416,789 teaches a synergistic combination of fungicides, including boron-containing compounds, organo-iodine compounds, and amine-oxides. U.S. Pat. No. 5,846,305 discloses a wood preservative composition comprising a copper compound, an amine solvent and a boron compound. U.S. Pat. No. 6,582,732 teaches a synergistic combination of insecticides including boron-containing compounds and synthetic pyrethroids. Also, a wood preservers are sold by Blackfriar, as a combination of trihexyleneglycol biborate (THGB) and naphta, for red cedar, by Triton as a paste combination of THGB and permethrin, by Palace as a combination of THGB and cypermethrin. These compositions are simple, two component, solvent based, preservative compositions and do not contain other or multiple organic fungicides, water repellants, or other compositions.

It is also known to use iodopropargyl derivatives such as 3-iodo-2-propynyl-n-butyl carbamate (IPBC) for protection against fungi which cause structural and cosmetic damage to wood. However, while effective, this compound used alone is expensive and requires larger amounts to achieve the desired end result. U.S. Pat. No. 5,389,300 provides a composition for protecting sawn timber against wood discoloring fungi, containing a phenol fungicide and an organo-iodine fungicide such as IPBC. Other fungicides, insecticides, or active ingredients, including boron compounds, can be added to the composition.

U.S. Pat. No. Re 36,798 provides a preservative composition for treatment of wood and other cellulosic materials, comprising a biocidal metal compound and a fungicidal compound containing a triazole group. Compositions of this invention may contain other organic fungicides, insecticides, or bacteriocides, including boron in any form, such as boric acid, boron, or boron esters. U.S. Pat. No. 4,950,685 relates to a wood preservative composition which provides stain resistance to wood. The composition comprises a synergistic combination of a quaternary ammonium compound and IPBC.

U.S. Pat. No. 5,990,043 relates to an anti-fouling composition which includes a carrier, a binder, and an effective amount of at least one insecticide, which can be a carbamate. Synergistic effects are observed when combinations of two or more of the numerous insecticides listed are used in combination.

A variety of insecticides, including creosote, chrome-copper-arsenate, organophosphates and boron compounds, are available to protect wood and wood composites against insect attack. Synthetic pyrethroids are also used to protect against pests but are not as economical or easy to use in the amounts needed for sufficient pest control. For example, U.S. Pat. Nos. 5,480,638 and 5,575,996 disclose a powdered insecticide bait composition comprised of pet food, powdered pyrethrin and boric acid. U.S. Pat. No. 5,516,620 relates to a controlled release composition in which a insecticide is encapsulated in a starch-borax-urea matrix. U.S. Pat. No. 5,880,142 discloses a composition suitable for controlling termites comprised of a compound of a specific chemical formula used in combination with a pyrethroid. U.S. Pat. No. 5,916,356 discloses a wood preservative composition comprising a synergistic combination of a biocidal metal compound and a fungicidal compound having a triazole group. The biocidal metal compound can be zinc in the form of an inorganic salt such as zinc borate.

The problem with combinations of preservatives, especially when combined in organic and waterborne solvents, is that they can be unpredictably unstable or have limited stability such that they must be used quickly once mixed or they have no or little "shelf life". As noted in U.S. Pat. No. 5,151, 127 which teaches a composition containing a fire retardant and wood preservation compounds, including boron and boron oxide compounds, "the component compounds of the compositions are mixed in specific sequences to avoid coagulation of the mixture."

SUMMARY OF THE INVENTION

The present invention is the result of the discovery that an organic solvent based wood preservative composition which is a mixture of fungicides and insecticides and which contains an borate fungicidal composition, which is soluble in an organic solvent, has surprising stability. The wood preservative composition of the present invention is a mixture of a fungicide which is a combination of trihexylene glycol biborate, an organo-iodine compound, triazole(s), water repellants, and a synthetic pyrethroid insecticide, where the fungicide and the insecticide are present in a sufficient amount that wood treated with the wood treatment material contains fungicide and insecticide in an amount of about 1 ppm to 5000 ppm, based on the weight of the wood after treatment, and, preferably, the boric acid equivalent present in the wood after treatment is in an amount of about 0.01% to 0.4% by weight based upon the weight of the wood.

DETAILED DESCRIPTION OF THE INVENTION

The present invention provides a wood treatment material composition which provides improved stability, which includes a combination of fungicides, including a boron-containing compound, an organo iodine compound or compounds, and a triazole compound, an insecticide, such as a synthetic pyrethroid, and an organic solvent or carrier, and optionally water repellants and/or other organic insecticides, and which provides improved resistance to insect attack on wood treated with this combination.

The fungicide will consist of boron-containing fungicide composition and organic fungicide. The organic fungicides include organo iodine (i.e. 3-iodo-2-proynyl-n-butyl carbamate), triazoles (i.e. tebuconazole and propriconazole), quaternary ammonium, organo tin (i.e. bis tributyl tin oxide, thiazoles (i.e. 2-(thiocyanomethylthio)benzothiazole), and are present in a combined total amount of about 0.1 wt/wt % to about 2.0 wt/wt %. i.e., weight percentage based upon the total weight of the mixture.

The optional water repellants that can be employed include petroleum slack and paraffin waxes and can be used in amounts of about 0.5 wt/wt % to 5.0 wt/wt %.

The organic insecticides employed include pyridine, organothiophosphate (i.e. chlorpyriphos), and synthetic pyrethroids (i.e. permethrin, cypermethrin) in amounts of about 0.0 wt/wt % to 0.2 wt/wt %.

As used herein, the term "boron-containing fungicide" includes fungicides containing at least one boron compound, such as boric acid esters, which are soluble in organic solvents and have sterically hindered di-alcohol and tri-alcohol groups, but do not contain an anhydride bond between the boron atoms, including, but not limited to, trihexylene glycol biborate, trioctylene glycol biborate, and triisopropanolamine borate. The preferred borate ester composition contains 5% or more, based upon the weight of the composition, of boron. The preferred boron-containing fungicide is trihexylene glycol biborate, which has a boron content of 5.84% by weight.

The term "organo-iodine compounds" refers to a category of organo-iodine compounds known to have biocidal activity and to provide protection against fungi when applied to wood and other materials. Examples of organo-iodine compounds which may be used in the present invention include, but are not limited to, iodopropargyl derivatives including compounds derived from propargyl or iodopropargyl alcohols such as the esters, ethers, acetals, carbamates and carbonates and the iodopropargyl derivatives of pyrimidines, thiazolinones, tetrazoles, triazinones, sulfamides, benzothiazoles, ammonium salts, carboxamides, hydroxamates, and ureas. Compounds of this type include iodopropargyl carbamates such as 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof. Preferred is 3-iodo-2-propynyl butyl carbamate (IPBC).

The organo-iodine compounds can be used alone or in combination with other active fungicides such as triazoles. The triazole compound may be any compound which contains a triazole group and which possesses biocidal activity. Preferably the triazole compound contains the triazole group. A preferred compound is tebuconazole: alpha-[2-(4-chlorophenyl)ethyl]-alpha(1,1-dimethylethyl)-1H-1,2,4-triazole-1-ethanol. Alternatively, the triazole compound can be propiconazole (1-[[2-(2,4-dichlorophenyl)-4-propyl-1,3-dioxolan-2-yl]methyl]-1H-1,2,4-triazole) and azaconazole (1-[[2,4-dichlorophenyl)-1,3-dioxolan-2-yl]methyl]-1H-1,2,4-triazole). Hexaconazole and difenaconazole are examples of further triazole compounds which may be used in the compositions of the invention. Compositions may contain more than one triazole compound for example, they may contain tebuconazole and propiconazole, or a mixture of tebuconazole, propiconazole and azaconazole.

The term "synthetic pyrethroid" includes a group of insect growth regulators or insecticides that act as neurotoxins and are especially effective against insects that are destructive in the adult stage. This class of insecticides is desirable for pest control because it is considered to be of low toxicity to animals and humans. However, it is desirable to use pyrethroids in combination with other insecticides due to their high cost. Suitable synthetic pyrethroids include deltamethrin, cyfluthrin, permethrin, tralomethrin, cypermethrin, resmethrin and other synthetic pyrethroids. A preferred synthetic pyrethroid is permethrin.

The term "wood" includes a variety of wood and wood-based materials, including but not limited to logs and other types of dried lumber, green lumber, fiberboards, strand board, laminated veneer lumber, cellulosic composites, plastic wood composites and other types of wood, wood composites and engineered wood formed from wood chips, strands, veneers and adhesives.

As used herein, the term "wood treatment material" refers to this combination of compositions, which may be used with other additives such as resins or solvents, and which is applied to wood by a variety of methods including, but not limited to, spraying, dipping, pressure treating, addition during formation of engineered wood, and other methods known to those skilled in the art that are used to apply such substances to wood.

In a method of creating the wood product, the wood treatment product can be applied on the surface of the wood, as in spraying or dipping the wood in an organic solvent solution containing all the boron containing wood preservative, the fungicide, and the insecticide. Typically, the organo-iodine compound and the amine-oxide compound are pre-mixed with solvents in a ratio of about 4 parts organo-iodine compound, 27 parts amine-oxide compound and 6 parts solvent (the remaining 63 parts consists of inactive material due to the manner of packaging active ingredients for sale). Any organic solvent can be used, but polar organic solvents are preferred as they will provide better solubilization of the organo-iodine compound. Most preferred are solvents such as dimethyl sulfoxide and dipropylene glycol.

On a weight to weight percent basis, the boron-containing compound will be present in the final wood product in an amount of about 0.01 wt. % to about 2.0 wt. %, preferably about 0.20 wt. % to about 1.0 wt. %. The organo-iodine compound will be present in the final wood product in an amount of between about 10 ppm and about 1000 ppm, preferably between about 20 and 100 ppm. The synthetic pyrethroid will be present in the final wood product in an amount of between about 1 ppm to about 1000 ppm, preferably between about 5 ppm and about 100 ppm. All weight percent or part-per-million values are based on the total weight of the wood product after treatment.

The insecticides can be applied on the surface of the wood, as in spraying or dipping the wood in a solution containing both insecticides. Other constituents of the solution include a paraffin wax emulsion and water. The insecticides can also be applied to the wood with pressure treatment that is commonly used on solid or engineered wood. A third method, particularly for engineered wood, is to treat the wood chips or strands with the insecticide combination in powder or liquid form prior to formation of the composite wood boards. Wood may be treated by more than one of these methods.

The wood treatment compositions of the present invention are made my mixing the fungicides and insecticides together in an appropriate solvent or carrier. The solvent is neutral and can comprise water, mineral spirits, or oils, with mineral spirits being preferred.

Compatibility Test:

Test A

In a 50 gallon pilot plant mixing tank, a commercially available fungicide (Fungicide I), which is a mixture of iodo-2-propynyl butyl carbamate (IPBC), tebuconazole, and propiconazole, and water repellants was mixed with a commercially available boron-containing fungicide (Fungicide II), which is a mixture of two borate esters, namely 1,4, tributylene glycol biborate, also known as 2,2'-((1-methyl-1,3-propanediyl)bis(oxy)) bis(4-methyldioxaborinane) or 1,3-butylene glycol biborate, and hexylene glycol biborate, also known as 2,2'-oxybis (4,4,6-trimethyl-1,3,2-dioxaborinane) or hexylene glycol boric anhydride. The IPBC mixture and the boron-containing mixtures were used in proportions to achieve a 90/10 by volume mixture, which was followed by an 88/12 mixture. When mixing, the mixture became hazy in appearance. After approximately one day into the pilot, a brownish/red bottom layer appeared and remained through the rest of the pilot. Yellow staining of the treated wood parts was seen on parts treated at the end of the third day of testing.

In a second test, Fungicide I was mixed with a commercially available insecticide, which is permethrin in an inert solvent, and that in turn was mixed with Fungicide II and diacetone alcohol as a co-solvent. The compositions were added resulting in a mixture of 85.11% Fungicide 1 and 8.51% Fungicide II, and 6.38% diacetone alcohol mixture by volume. The mixture had a slight hazy appearance, but less than that seen in the first test. The major portion of the testing was performed on the first day with occasional batches tested over the following two weeks. At the end of the two week pilot, the test mixture was stirred for sampling and it is at this time a separated bottom layer was noticed. The separated layer was not colored in appearance. The mixture was very hazing after stirring and separated readily upon standing.

The mixture from the first test was decanted and the bottom of the storage drum contained a white crystalline material along with the brownish/red separated layer.

Test B

A mixture of Fungicide I and a 10% tributylene glycol biborate (TBGB) was made by pouring the TBGB into the Fungicide I. The following observations were made while making and after making the mixture.

The TBGB reacted with moisture in the air while pouring and formed a thin white film over the pour stream. The mixture immediately became hazy during mixing. A brownish/red colored layer immediately began to form at the bottom of the container after completion of the mixing. Moisture from the air inside of the closed container was drawn into the mixture causing the container to collapse slightly after a week. This behavior was duplicated by opening the container and allowing it to come back to its normal shape and closing the container again. It is noted that TBGB in a fungicide mixture when open to the air will draw moisture from the air and hydrolyze to a form insolubles and result in an increase in the separated phase. The hazing during mixing and phase separation seen during the first test was identical to that observed during this mixing.

The TBGB test was repeated using a mixture of 10% hexylene glycol biborate (HGB). The mixture was made by pouring the HGB into the Fungicide I composition. The following observations were made while making and after making the mixture:

The mixture remained clear during mixing. An opaque white crystalline material immediately formed on the container surfaces and continued to grow in volume until equilibrium was reached after several days. The container was closed. The crystalline material is soluble in water and isopropyl alcohol. A 10% HGB/mineral spirits solution was made to test for moisture adsorption from the air. The solution remained clear without separation or solid precipitation while the container was closed. Opening the container to air resulted in white crystal formation after setting over night. The crystalline material is likely the hydroxy hexylene glycol borate compound formed by hydrolysis of the anhydride bond. The crystal formation in the HGB testing is similar to that observed in the first test in the test mixture storage drum.

The basic observations are that both the TBGB and HGB react with various components of the Fungicide I mixture and react with moisture in the air. Both esters are too reactive to form stable mixtures with Fungicide I.

A mixture of tri hexylene glycol biborate (THGB) and Fungicide I was made. It was observed that the solution remains clear with no separation. Next, the mixture was left open to atmosphere for 90 days at 40% to 50% relative humidity conditions. The solution remained clear with no separation and no precipitation of solids. A 10% evaporative loss of mineral spirits approximately every 14 days was replaced with new mineral spirits without any negative effects. A plastic container of the mixture was closed for 18 days without any collapse of the container. The mixture was placed in a 0° F. freezer overnight. When removed from the freezer, white solids were observed at the bottom of the container. Heating the mixture to approximately 20 F with stirring dissolved all of the white solids. The mixture was placed in a 42° F. refrigerator for 63 hours. The mixture remained clear without separation or precipitation.

As can be seen, the use of THGB in Fungicide mixtures produces stable mixtures, when compared to the use of other organic boron-containing fungicides.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of the true scope and breadth of the invention, reference should be made to the following claims.

What is claimed is:

1. A wood preservative composition comprising a mixture of a fungicide, which is a mixture of trihexylene glycol biborate in an organic solvent, one or more iodopropargyl carbamates, and one or more triazoles, and a synthetic pyrethroid insecticide, said fungicide and insecticide being present in sufficient amount that wood treated with the wood preservative composition contains the fungicide and insecticide in an amount of about 1 ppm to 5,000 ppm, based on the weight of the wood after treatment.

2. The composition of claim 1 wherein the trihexylene glycol biborate is present in an amount of about 0.5 to 30.0 wt % based upon the weight of the total mixture.

3. The composition of claim 1 wherein the trihexylene glycol biborate is present in an amount of about 3.0 to 20.0 wt % based upon the weight of the total mixture.

4. The composition of claim 1 wherein the synthetic pyrethroid is selected from the group consisting of deltamethrin, permethrin, cyfluthrin, tralomethrin, cypermethrin and resmethrin.

5. The composition of claim 1 wherein the synthetic pyrethroid is permethrin.

6. The composition of claim 1 wherein the one or more iodopropargyl carbamates is selected from the group consisting of 3-iodo-2-propynyl propyl carbamate, 3-iodo-2-propynyl butyl carbamate, 3-iodo-2-propynyl hexyl carbamate, 3-iodo-2-propynyl cyclohexyl carbamate, 3-iodo-2-propynyl phenyl carbamate, and mixtures thereof.

7. The composition of claim 1 wherein the one or more iodopropargyl carbamates is 3-iodo-2-propynyl butyl carbamate.

8. The composition of claim 1 wherein the triazole fungicide is selected from the group consisting of tebuconazole, propiconazole, azaconazole, hexaconazole, difenaconzole, and mixtures thereof.

9. The composition of claim 1 wherein the wood preservative composition further includes a water repellant.

10. The composition of claim 1 wherein the trihexylene glycol biborate is present in an amount such that wood treated with the wood treatment composition has a boric acid equivalent in an amount of about 0.1% to 0.4% by weight based upon the weight of the wood.

11. A wood treated with the wood preservative composition of claim.

12. A wood treated with the wood preservative composition of claim 1 wherein said synthetic pyrethroid is present in the wood in an amount of about 1 ppm to 1000 ppm, based on weight of the wood after treatment.

13. A wood treated with the wood preservative composition of claim 1 wherein said fungicide and the insecticide is present in a sufficient amount that wood treated with the wood preservative composition contains fungicide and insecticide in an amount of about 1 ppm to 5000 ppm, based on the weight of the wood after treatment and has a boric acid equivalent in an amount of about 0.01% to 0.4% by weight based upon the weight of the wood.

14. The composition of claim 1 wherein the triazole fungicide comprises a mixture of tebuconazole and propiconazole.

15. The composition of claim 1 wherein:
(a) the pyrethroid is permethrin;
(b) the one or more iodopropargyl carbamate is 3-iodo-2-propynyl butyl carbamate; and
(c) the triazole fungicide is a mixture of tebuconazole and propiconazole.

* * * * *